United States Patent [19]

Child et al.

[11] 4,235,996
[45] Nov. 25, 1980

[54] BIS(2-IMIDAZOLIN-2-YLHYDRAZONE)-9,10-DIHYDRO-9,10-ANTHRACENEDICARBOXALDEHYDES

[75] Inventors: Ralph G. Child, Pearl River; Stanley A. Lang, Jr., Stony Point; Ving J. Lee, Airmont; Yang-I Lin, Nanuet, all of N.Y.

[73] Assignee: American Cyanamid Company, Stamford, Conn.

[21] Appl. No.: 943,908

[22] Filed: Sep. 19, 1978

[51] Int. Cl.³ .............. C07C 143/72; C07C 153/00; C07D 233/16
[52] U.S. Cl. .............................. 542/415; 260/455 A; 560/25; 560/28; 564/86; 564/251

[58] Field of Search ............... 542/415; 260/566 B, 260/564 F, 455 A, 552 SC, 554, 556 AR; 560/25, 28

[56] References Cited

PUBLICATIONS

Finar, Organic Chemistry, Longmans Green & Co., London, 1963, pp. 152–153.

Primary Examiner—Arthur P. Demers
Attorney, Agent, or Firm—Edward A. Conroy, Jr.

[57] ABSTRACT

This disclosure describes 9,10-dihydroanthracene-9,10-dicarboxaldehyde-bis-hydrazones and derivatives thereof useful as antibacterial agents, for inhibiting the growth of transplanted mouse tumors, and for inducing the regression and/or palliation of leukemia and related cancers in mammals.

19 Claims, No Drawings

BIS(2-IMIDAZOLIN-2-YLHYDRAZONE)-9,10-DIHYDRO-9,10-ANTHRACENEDICARBOXALDEHYDES

BRIEF SUMMARY OF THE INVENTION

This invention relates to new organic compounds and, more particularly, is concerned with novel 9,10-dihydroanthracene-9,10-dicarboxyaldehyde-bis-hydrazones which may be represented by the following general formula:

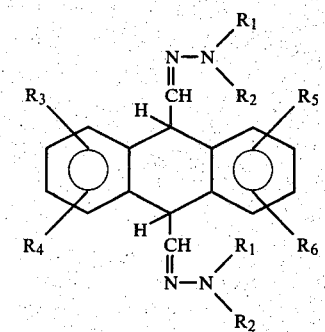 (I)

wherein $R_1$ is hydrogen or alkyl having up to 4 carbon atoms; $R_2$ is hydrogen, alkyl having up to 4 carbon atoms, phenyl or a moiety of the formulae:

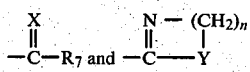

wherein n is 2, 3, 4, or 5, $R_7$ is amino, anilino, hydrazino, monohydroxyalkylamino having from 2 to 4 carbon atoms and wherein the carbon atom alpha to the nitrogen atom may not bear an hydroxy group, alkylamino having up to 4 carbon atoms, dialkylamino wherein each alkyl group has up to 4 carbon atoms, cycloalkylamino having from 3 to 6 carbon atoms, benzylamino, α-phenethylamino, β-phenethylamino, 2-furfurylamino, 3-furfurylamino, α-thenylamino, β-thenylamino, α-pyridylmethylamino, β-pyridylmethylamino, γ-pyridylmethylamino, indanylamino, pyrrolidino, piperidino, morpholino, thiomorpholino, N-methylpiperazino, alkoxy having up to 4 carbon atoms or alkylthio having up to 4 carbon atoms, X is oxo (O=), thioxo (S=) or imino (R—N= wherein R is hydrogen or alkyl having up to 4 carbon atoms) and Y is oxy (—O—), thio (—S—) or a divalent group of the formula:

wherein $R_8$ is hydrogen, alkyl having up to 4 carbon atoms or monohydroxyalkyl having from 2 to 4 carbon atoms and wherein the carbon atom alpha to the nitrogen atom may not bear an hydroxy group; and $R_3$, $R_4$, $R_5$ and $R_6$ are each individually selected from the group consisting of hydrogen, halogen (F, Cl, Br, I), hydroxy, nitro, amino, sulfonamido, alkyl having up to 4 carbon atoms and alkoxy having up to 4 carbon atoms.

The hydrazono substituents pendant from the anthracene-9,10-bis-carbonyl nuclei may be the same or different and may be in the syn or anti forms. Additionally, the entire units

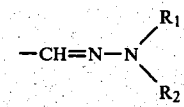

at the $C_9$ and $C_{10}$ positions may be either cis (both extending out from the same face of the anthracene nucleus) or trans (extending out from the opposite faces of the anthracene nucleus).

A preferred embodiment of the present invention consists of compounds which may be represented by the following structural formula:

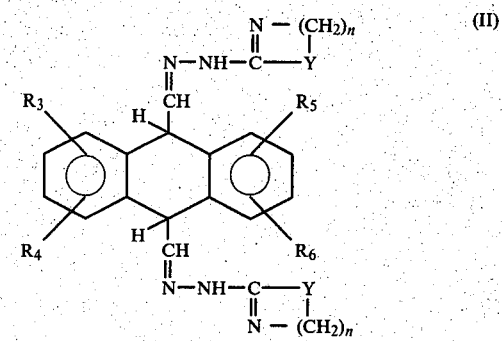 (II)

wherein n, Y, $R_3$, $R_4$, $R_5$ and $R_6$ are as hereinabove defined.

DETAILED DESCRIPTION OF THE INVENTION

The novel compounds of the present invention are obtainable as yellow crystalline materials having characteristic melting points and absorption spectra and which may be purified by recrystallization from common organic solvents such as lower alkanols, dimethylformamide, tetrahydrofuran, methyl isobutyl ketone, and the like.

The organic bases of this invention form non-toxic acid-addition and quaternary ammonium salts with a variety of pharmacologically acceptable organic and inorganic salt-forming reagents. Thus, acid-addition salts, formed by admixture of the organic free base with one or more equivalents of an acid, suitably in a neutral solvent, are formed with such acids as sulfuric, phosphoric, hydrochloric, hydrobromic, sulfamic, citric, lactic, malic, succinic, tartaric, acetic, benzoic, gluconic, ascorbic, and the like. Quaternary ammonium salts may be formed by reaction of the free bases with one or more equivalents of a variety of organic esters of sulfuric, hydrohalic and aromatic sulfonic acids. The organic reagents employed for quaternary ammonium salt formation are preferably lower alkyl halides. However, other organic reagents are suitable for quaternary ammonium salt formation, and may be selected from among a diverse class of compounds including benzyl chloride, phenethyl chloride, naphthylmethyl chloride, dimethyl sulfate, methyl benzenesulfonate ethyl toluenesulfonate, allyl chloride, methallyl bromide and crotyl bromide. For purposes of this invention the free bases are equivalent to their non-toxic acid-addition and quaternary ammonium salts. The acid-addition and quaternary ammonium salts of the organic bases of the present invention are, in general, crystalline solids, relatively soluble in water, methanol and ethanol but relatively insoluble in non-polar organic solvents such as diethyl ether, benzene, toluene, and the like.

The novel compounds of the present invention possess the property of inhibiting the growth of transplanted mouse tumors as established by the following tests.

Lymphocytic leukemia P388 test

The animals used are mice, all of one sex, weighing a minimum of 18 g. and all within a 3 gram weight range. There are 5 or 6 animals per test group. The tumor transplant is by intraperitoneal injection of 0.1 ml. or 0.5 ml. of dilute ascitic fluid containing $10^6$ cells of lymphocytic leukemia p388. The test compounds are administered intraperitoneally on days one, 5 and 9 (relative to tumor inoculation) at various doses. The animals are weighed and survivors are recorded on a regular basis for 60 days. The median survival time and the ratio of survival time for treated (T)/control (C) animals are calculated. The positive control compound is 5-fluorouracil given as an intraperitoneal injection on days one, 5 and 9. The results of this test with representative compounds of the present invention appear in Table I below. The criterion for efficacy is $T/C \times 100 \geq 125\%$.

TABLE I

| Lymphocytic Leukemia P388 Test | | | |
|---|---|---|---|
| Compound | Dose (mg./kg.) | Median Survival (Days) | T/C × 100 (Percent) |
| Bis(2-imidazolin-2-ylhydrazone)-9,10-dihydro-9,10-anthracenedicarboxaldehyde dihydrochloride | 12.5 | 16 | 152 |
|  | 6.25 | 13 | 129 |
| Control | — | 10.5 | — |
| 5-Fluorouracil | 40 | 19.0 | 181 |
| Bis(2-imidazolin-2-ylhydrazone)-9,10-dihydro-9,10-anthracenedicarboxaldehyde | 400 | 25 | 227 |
|  | 200 | 23 | 209 |
|  | 100 | 19.5 | 177 |
|  | 50 | 20 | 182 |
|  | 25 | 17.5 | 159 |
|  | 12.5 | 16.5 | 150 |
|  | 6.25 | 16.5 | 150 |
|  | 3.12 | 14 | 127 |
| 5-Fluorouracil | 40 | 18 | 164 |
| Control | — | 11 | — |
| 1-Chloro-bis(2-imidazolin-2-ylhydrazone)-9,10-dihydro-9,10-anthracenedicarboxaldehyde | 25 | 21.0 | 221 |
|  | 12.5 | 19.5 | 205 |
|  | 6.25 | 16.5 | 174 |

TABLE I-continued

| Lymphocytic Leukemia P388 Test | | | |
|---|---|---|---|
| Compound | Dose (mg./kg.) | Median Survival (Days) | T/C × 100 (Percent) |
| dihydrochloride | 3.12 | 15.5 | 163 |
| Control | 0 | 9.5 |  |
| 5-Fluorouracil | 60 | 15.0 | 158 |
| 2-Methyl-bis(2-imidazolin-2-ylhydrazone)-9,10-dihydro-9,10-anthracenedicarboxaldehyde dihydrochloride | 50 | 19.0 | 200 |
|  | 25 | 16.0 | 168 |
|  | 12.5 | 16.0 | 168 |
|  | 6.25 | 14.5 | 153 |
|  | 3.12 | 13.5 | 142 |
| Control | 0 | 9.5 |  |
| 5-Fluorouracil | 60 | 15.0 | 158 |
| 2-Chloro-bis(2-imidazolin-2-ylhydrazone)-9,10-dihydro-9,10-anthracenedicarboxaldehyde dihydrochloride | 50 | 20.0 | 200 |
|  | 25 | 18.0 | 180 |
|  | 12.5 | 18.0 | 180 |
|  | 6.25 | 18.5 | 185 |
|  | 3.12 | 17.5 | 175 |
| Control | 0 | 10.0 |  |
| 5-Fluorouracil | 60 | 18.5 | 185 |

Melanotic Melanoma B16

The animals used are C57BC/6 mice, all of the same sex, weighing a minimum of 17 g. and all within a 3 g. weight range. There are normally 10 animals per test group. A one-gram portion of melanotic melanoma B16 tumor is homogenized in 10 ml. of cold balanced salt solution and a 0.5 ml. aliquot of the homogenate is implanted intraperitoneally into each of the test mice. The test compounds are administered intraperitoneally on days one through 9 (relative to tumor inoculation) at various doses. The animals are weighed and survivors are recorded on a regular basis for 60 days. The median survival time and the ratio of survival time for treated (T)/control (C) animals are calculated. The positive control compound is 5-fluorouracil given as a 20 mg./kg. injection. The results of this test with representative compounds of the present invention appear in Table II below. The criterion for efficacy is $T/C \times 100 \geq 125\%$.

TABLE II

| Melanotic Melanoma B16 | | | |
|---|---|---|---|
| Compound | Dose (mg./kg.) | Median Survival (Days) | T/C × 100 (Percent) |
| 2-Methyl-bis(2-imidazolin-2-ylhydrazone)-9,10-dihydro-9,10-anthracenedicarboxaldehyde dihydrochloride | 12 | 33.5 | 197 |
|  | 6 | 28.0 | 165 |
|  | 3 | 25.0 | 147 |
|  | 1.5 | 24.0 | 141 |
| Control | 0 | 17.0 |  |
| 5-Fluorouracil | 20 | 28.5 | 168 |
| 1-Chloro-bis(2-imidazolin-2-ylhydrazone)-8,10-dihydro-9,10-anthracenedicarboxaldehyde dihydrohloride | 12 | 31.0 | 182 |
|  | 6 | 25.5 | 150 |
|  | 3 | 22.0 | 129 |
| Control | 0 | 17.0 |  |
| 5-Fluorouracil | 20 | 28.5 | 168 |
| Bis(2-imidazolin-2-ylhydrazone-9,10-anthracenedicarboxaldehyde dihydrochloride | 12 | 32.0 | 200 |
|  | 6 | 25.0 | 156 |
|  | 3 | 22.0 | 138 |
|  | 1.5 | 21.0 | 131 |
| Control | 0 | 16.0 |  |
| 5-Fluorouracil | 20 | 30 | 187 |

The novel compounds of the present invention exhibit antibacterial activity when tested according to the following procedure. The antibacterial spectrum, in terms of the concentration required to inhibit the growth of various typical bacteria, was determined in a standard manner by the agar-dilution streak-plate technique. A Steers multiple inocula replicator was used with incubation at 37° C. for 18 hours in Mueller-Ninton agar. The results for typical compounds of this invention are set forth in Table III below as the minimal inhibitory concentration in micrograms per milliliter,

TABLE III

| | Test Organism Minimal Inhibitory Concentration (mcg./ml.) | | | |
|---|---|---|---|---|
| Compound | Staphylococcus aureus OSU 75-2 | Staphylococcus aureus Q 74-11 | Staphylococcus aureus St. Paul (NYC 78-1) | Enterococcus SM 77-15 |
| Bis-(2-imidazolin-2-ylhydrazone)-9,10-dihydro-9,10-anthracene-dicarboxaldehyde | 128 | 32 | 64 | 16 |
| 1,4-Dimethoxy-bis-(2-imidazolin-2-ylhydrazone)-9,10-dihydro-9,10-anthracenedicarboxaldehyde | 128 | 64 | 128 | 256 |
| 1,4-Dimethoxy-bis-(2-imidazolin-2-ylhydrazone)-9,10-dihydro-9,10-anthracenedicarboxaldehyde dihydrochloride | 128 | 128 | 128 | 256 |

The modes contemplated for administration are essentially parenteral and intraperitoneal. Solutions of the active ingredient as a free base or salt can be prepared in water or in water suitably mixed with, for example, surfactants such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical compositions can be in forms suitable for injectable use, which forms include sterile aqueous solutions or dispersions and sterile powders for the extemporanous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active ingredient or ingredients in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatable with the active ingredient, its use in the present compositions is contemplated. Supplementary active ingredients can also be incorporated into the inventive compositions.

It is especially advantageous to formulate compositions in dosage unit form for ease of administration and uniformity of dosage. Dosage unit form as used in the specification and claims herein refers to physically discrete units suited as unitary dosages for the animal subjects to be treated, each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as disclosed in detail in this specification.

The dosage of the principal active ingredient for the treatment of the indicated conditions depends upon the age, weight and condition of the subject being treated; the particular condition and its severity; the particular form of the active ingredient and the route of administration. A daily dose of from about one to about 100 mg./kg. of body weight given singly or in divided doses of up to 5 times a day embraces the effective range for the treatment of most conditions for which the novel compounds are effective and substantially non-toxic. For a 75-kg. subject, this translates into between about 75 and about 7500 mg./day. If the dosage is divided, for example, into 3 individual dosages, these will range from about 25 to about 2500 mg. of the active ingredient. The preferred range is from 2 to about 50 mg./kg. of body weight/day with about 2 to about 30 mg./kg./day being more preferred.

The principal active ingredient is compounded for convenient and effective administration in effective amounts with a suitable pharmaceutically-acceptable carrier in dosage unit form as hereinbefore disclosed. A unit dosage form can, for example, contain the principal active ingredient in amounts ranging from about 0.1 to about 400 mg., with from about one to about 30 mg. being preferred. Expressed in proportions, the active ingredient is generally present in from about 0.1 to about 400 mg./ml. of carrier. In the case of compositions containing supplementary active ingredients, the dosages are determined by reference to the usual dose and manner of administration of the said ingredients.

The novel compounds of the present invention may be readily prepared as set forth in the following reaction scheme:

sium periodate and stirred at room temperature for 24 hours to provide the dicarboxaldehydes (VI). Either procedure provides the cis-isomer of the dicarboxaldehydes (VI) which may be readily converted to the trans form by standard procedures. Treatment of the dicarboxaldehydes (VI) with a hydrazine of the formula

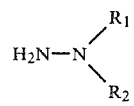

in ethanol or n-propanol at the reflux temperature for 1–4 hours provides the 9,10-bis-hydrazones (I).

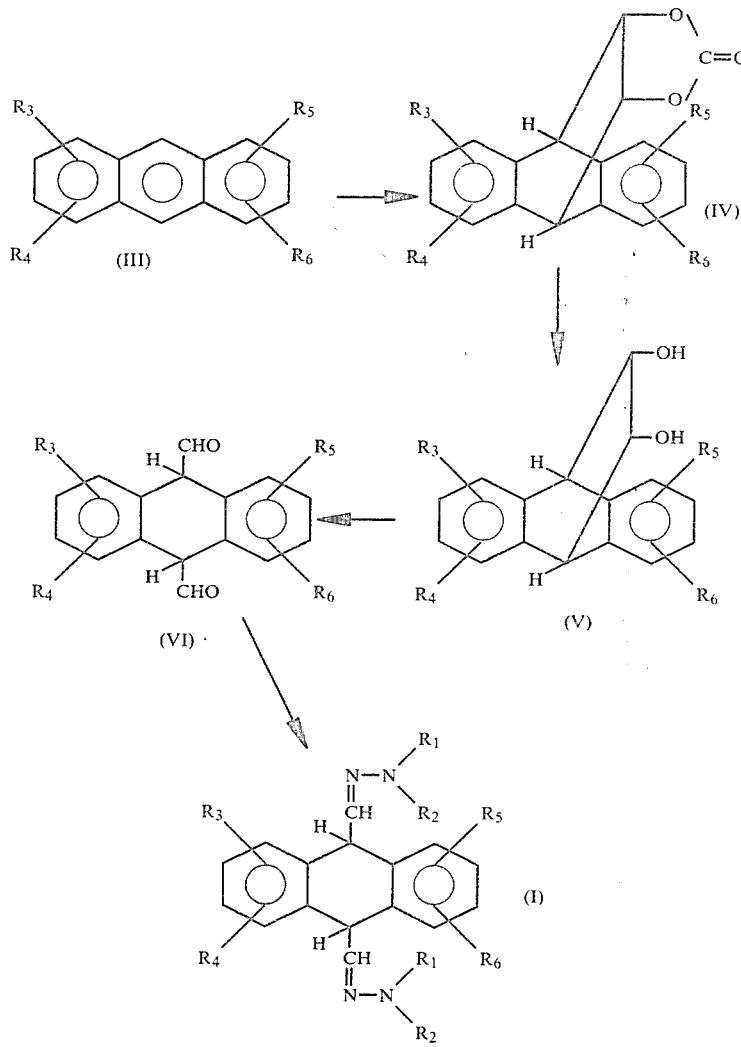

wherein $R_1$, $R_2$, $R_3$, $R_4$, $R_5$ and $R_6$ are as hereinabove defined. In accordance with the above reaction scheme, the anthracene derivative (III) is heated with excess vinylene carbonate under reflux for about 10–24 hours to give the cyclic carbonate (IV). Hydrolysis of the cyclic carbonate (IV) with aqueous-ethanolic potassium hydroxide at 70°–75° C. for about 1–4 hours produces the diol (V) which in turn is treated with lead tetraacetate in acetic acid at 20°–35° C. for about 1–2 hours to give the 9,10-dihydro-9,10-anthracenedicarboxaldehyde (VI). Alternatively, the diols (V) may be suspended in an aqueous solution of either sodium or potas- The invention will be described in greater detail in conjunction with the following specific examples.

EXAMPLE 1

9,10-Dihydro-9,10-anthracenedicarboxaldehyde

A mixture of 21.3 g. of vinylene carbonate (redistilled to give a colorless liquid 71°–73° C., 28 mm.) and 4.4 g. of dry anthracene is heated at reflux (165°–170° C.), under nitrogen for 20 hours and then vacuum distilled (62°–64° C., 17 mm.), leaving 10.2 g. of tan residue. This residue is taken up in 100 ml. of methylene chloride, treated with charcoal and filtered. The filtrate is treated with 100 ml. of methanol and cooled giving colorless crystals of cis-9,10-dihydro-9,10-ethanoanthracene-11,12-diol, cyclic carbonate (m.p. 260°-262° C.).

A mixture of 5.6 g. of cis-9,10-dihydro-9,10-ethanoanthracene-11,12-diol, cyclic carbonate, 4.9 g. of potassium hydroxide, 6.4 ml. of water and 53 ml. of ethanol is stirred at 70°-75° C. for 2 hours. The resulting two layer system is filtered. The filtrate is diluted with twice its volume of water and cooled producing colorless crystals of cis-9,10-dihydro-9,10-ethanoanthracene-11,12-diol (m.p. 202°-204° C.).

A mixture of 2.38 g. of cis-9,10-dihydro-9,10-ethanoanthracene-11,12-diol in 40 ml. of glacial acetic acid at room temperature is treated portionwise with 4.8 g. of lead tetraacetate, with stirring over a period of 10 minutes. The mixture is cooled to 15° C. and the solid which forms is collected by filtration, washed once with glacial acetic acid, then thoroughly with water giving the desired product as colorless grains, m.p. 144°-146° C.

EXAMPLE 2

Cis-1,4-Dimethoxy-9,10-dihydro-9,10-anthracenedicarboxaldehyde

One gram of 1,4-dimethoxy-9,10-dihydro-9,10-ethanoanthracene-11,12-diol, is suspended in 30 ml. of an aqueous solution containing 0.77 g. of potassium periodate and one ml. of ethanol. After stirring at room temperature for 24 hours the insoluble material is removed by filtration, washed well with water and dried leaving a yellow product, m.p. 129°-132° C.

EXAMPLE 3

Bis(2-imidazolin-2-ylhydrazone)-9,10-dihydro-9,10-anthracenedicarboxaldehyde

A mixture of 2.36 g. of 9,10-dihydro-9,10-anthracenedicarboxaldehyde and 3.46 g. of 2-hydrazinoimidazoline dihydrochloride in 200 ml. of n-propanol is boiled on a hot plate for 1½ hours, concentrating the volume to 100 ml. The mixture is cooled and allowed to stand overnight, giving a solid which is collected by filtration, washed with n-propanol and dried. A 0.4 g. portion of this solid is recrystallized from water giving the desired dihydrochloride product as colorless flakes, m.p. 258°-262° C.

EXAMPLE 4

2-Chloro-9,10-dihydro-9,10-anthracenedicarboxaldehyde

A solution of 15.0 g. of 2-chloroanthracene in 60.8 g. of vinylene carbonate is refluxed for 20 hours and then vacuum distilled. The residue is recrystallized from methylene chloride-methanol giving cis-2-chloro-9,10-dihydro-9,10-ethanoanthracene-11,12-diol, cyclic carbonate as gray crystals, m.p. 200°-230° C.

A mixture of 12.0 g. of cis-2-chloro-9,10-dihydro-9,10-ethanoanthracene-11,12-diol, cyclic carbonate, 9.2 g. of potassium hydroxide, 12 ml. of water and 100 ml. of ethanol is heated at 75° C. for 2 hours and then evaporated in vacuo to 50 ml. The concentrate is diluted with 400 ml. of water and the resulting solid is collected by filtration. This solid is recrystallized from toluene, decolorizing with a small amount of charcoal, giving colorless crystals of cis-2-chloro-9,10-dihydro-9,10-ethanoanthracene-11,12-diol, m.p. 195°-210° C.

To a solution of 2.7 g. of cis-2-chloro-9,10-dihydro-9,10-ethanoanthracene-11,12-diol in 20 ml. of acetic acid at room temperature is added 5.0 g. of lead tetraacetate (containing 10% acetic acid) portionwise. The mixture is stirred for 10 minutes, cooled in an ice-water bath and the crystals which form are collected by filtration and washed with cold acetic acid, giving the desired product as off-white crystals, m.p. 113°-115° C.

EXAMPLE 5

2-Chloro-bis(2-imidazolin-2-ylhydrazone)-9,10-dihydro-9,10-anthracenedicarboxaldehyde dihydrochloride A reaction mixture comprising 0.7 g. of 2-chloro-9,10-dihydro-9,10-anthracenedicarboxaldehyde and 0.88 g. of 2-hydrazinoimidazoline dihydrochloride in 20 ml. of n-propanol is refluxed for one hour, during which time about 10 ml. of n-propanol is removed through a reflux condenser. The mixture is cooled and ether is added giving the desired product as yellow crystals, m.p. 190° C. (dec.).

EXAMPLE 6

1-Chloro-9,10-dihydro-9,10-anthracenedicarboxaldehyde

A mixture of 29.5 g. of 1-chloroanthracene and 126 g. of vinylcarbonate is reacted as described in Example 4, giving tan crystals of cis-1-chloro-9,10-dihydro-9,10-ethanoanthracene-11,12-diol, cyclic carbonate, m.p. 242°-250° C.

A reaction mixture comprising 27.9 g. of cis-1-chloro-9,10-dihydro-9,10-ethanoanthracene-11,12-diol, cyclic carbonate, 21.4 g. of potassium hydroxide, 28 ml. of water and 230 ml. of ethanol is heated at 75° C. for 2 hours and then evaporated in vacuo to 80 ml. The residue is dissolved in 500 ml. of chloroform. The chloroform solution is washed with three 70 ml. portions of water and decolorized with charcoal. The chloroform is removed and the yellow residue is dissolved in 150 ml. of toluene. On cooling the product cis-1-chloro-9,10-dihydro-9,10-ethanoanthracene-11,12-diol is collected as colorless crystals, m.p. 180°-182° C.

To a solution of 0.54 g. of cis-1-chloro-9,10-dihydro-9,10-ethanoanthracene-11,12-diol in 5 ml. of acetic acid at 35° C. is added 1.0 g. of lead tetraacetate, portionwise. The mixture is stirred for 10 minutes, cooled in an ice-water bath and the crystals which form are collected by filtration and washed with cold acetic acid, giving the desired product as colorless crystals, m.p. 144°-146° C.

EXAMPLE 7

1-Chloro-bis(2-imidazolin-2-ylhydrazone)-9,10-dihydro-9,10-anthracenedicarboxaldehyde dihydrochloride A reaction mixture comprising 3.7 g. of 1-chloro-9,10-dihydro-9,10-anthracenedicarboxaldehyde and 4.64 g. of 2-hydrazinoimidazoline dihydrochloride in 100 ml. of n-propanol is refluxed for one hour, during which time about 50 ml. of n-propanol is removed through a reflux condenser. The mixture is cooled and ether is added giving the desired product as yellow crystals, m.p. 200° C. (dec.).

EXAMPLE 8

2-Methyl-9,10-dihydro-9,10-anthracenedicarboxaldehyde

A 10 g. portion of 2-methylanthracene in 50 ml. of vinylene carbonate is heated to reflux under nitrogen for 20 hours. The excess vinylene carbonate is removed by vacuum distillation (55° C., 11–12 mm.) and the residue is taken up in 100 ml. of methylene chloride, filtered and triturated with three times its volume of methanol. The product, cis-2-methyl-9,10-dihydro-9,10-ethanoanthracene-11,12-diol, cyclic carbonate is recovered in its syn and anti forms as cream colored crystals, (m.p. 225°–227° C. and 183°–185° C.).

A 2.8 g. portion of one of the syn and anti forms of cis-2-methyl-9,10-dihydro-9,10-ethanoanthracene-11,12-diol, cyclic carbonate (m.p. 225°–227° C.) in a mixture of 2.5 g. of potassium carbonate, 2.3 ml. of water and 27 ml. of ethanol is stirred at 70° C. for 2 hours. The mixture is treated with three times its volume of water giving the corresponding syn or anti form of cis-2-methyl-9,10-dihydro-9,10-ethanoanthracene-11,12-diol as pale yellow crystals, (m.p. 227°–228° C.).

A 7.4 g. portion of the other syn or anti form of cis-2-methyl-9,10-dihydro-9,10-ethanoanthracene-11,12-diol cyclic carbonate (m.p. 183°–185° C.) in a mixture of 6.15 g. of potassium hydroxide, 8.1 ml. of water and 70 ml. of ethanol is reacted as described immediately above giving the corresponding syn or anti form of cis-2-methyl-9,10-dihydro-9,10-ethanoanthracene-11,12-diol as a cream colored solid, (m.p. 153°–156° C.)

A 2.5 g. portion of cis-2-methyl-9,10-dihydro-9,10-ethanoanthracene-11,12-diol [obtained above as yellow crystals (m.p. 227°–228° C.)] is suspended in 100 ml. of an aqueous solution containing 2.14 g. of sodium periodate and one ml. of ethanol. The mixture is stirred at room temperature for 2 hours and the solid is collected by filtration, washed with water and dried giving the desired product as a pale yellow solid, m.p. 125°–126° C.

EXAMPLE 9

2-Methyl-bis(2-imidazolin-2-ylhydrazone)-9,10-dihydro-9,10-anthracenedicarboxaldehyde dihydrochloride A mixture of 1.9 g. of 2-methyl-9,10-dihydro-9,10-anthracenedicarboxaldehyde and 2.63 g. of 2-hydrazinoimidazoline dihydrochloride in 150 ml. of n-propanol is heated to boiling and concentrated to about 50 ml. over the course of 1–2 hours, filtered while hot and then cooled. A 2–3 ml. portion of acetone and 200 ml. of ether are added giving a precipitate which is collected by filtration giving the desired product as a yellow solid, m.p. 210°–220° C. (dec.).

EXAMPLE 10

2,3-Dimethyl-9,10-dihydro-9,10-anthracene dicarboxaldehyde

A mixture of 35.4 g. of vinylene carbonate and 8.5 g. of 2,3-dimethylanthracene[(a)] is heated at reflux under nitrogen for 20 hours. The cooled solution is treated with 100 ml. of methanol, warmed, decolorized with charcoal, filtered and cooled giving 7.1 g. of colorless crystals (m.p. 207°–212° C.) of 2,3-dimethyl-9,10-dihydro-9,10-ethanoanthracene-11,12-diol, cyclic carbonate.
(a) Jaylord, N. G., Stepan. V., Collect. Czeck. Chem. Comm. 39, 1700(1974).

A mixture of 6.4 g. of 2,3-dimethyl-9,10-dihydro-9,10-ethanoanthracene-11,12-diol, cyclic carbonate, 5 g. of potassium hydroxide, 6.6 ml. of water and 60 ml. of ethanol is stirred at room temperature for 56 hours. The formed precipitate is filtered, dissolved in glacial acetic acid and precipitated with excess water giving 4.0 g. of colorless 2,3-dimethyl-9,10-dihydro-9,10-ethanoanthracene-11,12-diol, (m.p. 240°–245° C.).

A suspension of 0.3 g. of 2,3-dimethyl-9,10-dihydro-9,10-ethanoanthracene-11,12-diol in 10 ml. water and 0.1 ml. of ethanol is treated with 0.243 g. of sodium periodate and stirred at 20° for 2.5 hours. The formed solid is filtered, washed with water and dried giving 0.2 g. of 2,3-dimethyl-9,10-dihydro-9,10-anthracene dicarboxaldehyde, (m.p. 113°–117° C.).

EXAMPLE 11

2,3-Dimethyl-bis(2-imidazolin-2-ylhydrazone)-9,10-dihydro-9,10-anthracenedicarboxaldehyde dihydrochloride A mixture of 0.2 g. of 2,3-dimethyl-9,10-dihydro-9,10-anthracenedicarboxaldehyde and 0.3 g. of 2-hydrazinoimidazoline dihydrochloride in 30 ml. of n-propanol is boiled for 2 hours while concentrating to 10 ml. The yellow solution is treated with 0.5 ml. of acetone and 20 ml. of ether giving a yellow precipitate which was filtered, washed with acetone and dried leaving 0.15 g. of product (m.p. 285°–290° C.).

EXAMPLE 12

1,4-Dimethyl-9,10-dihydro-9,10-anthracenedicarboxaldehyde

A mixture of 4.12 g. of 1,4-dimethylanthracene and 17.2 g. of vinylene carbonate is refluxed under nitrogen for 18 hours, cooled, treated with four folumes of methanol, stirred and cooled. The formed crystals are filtered, washed with methanol and dried leaving 5.45 g. of colorless 1,4-dimethyl-9,10-dihydro-9,10-ethanoanthracene-11,12-diol, cyclic carbonate (m.p. 225°–245° C.).

A mixture of 4.4 g. of 1,4-dimethyl-9,10-dihydro-9,10-ethanoanthracene-11,12-diol, cyclic carbonate, 3.45 g. of potassium hydroxide, 4.5 ml. of water and 40 ml. of ethanol is stirred at 20° for 16 hours. The two layered mixture is filtered through Celite and treated with four volumes of water giving 3.8 g. of colorless 1,4-dimethyl-9,10-dihydro-9,10-ethanoanthracene-11,12-diol (m.p. 158°–160° C.).

A mixture of 1.5 g. of 1,4-dimethyl-9,10-dihydro-9,10-ethanoanthracene-11,12-diol and 1.22 g. of sodium periodate in 50 ml. of water and one ml. of ethanol is stirred for two hours at 20°. The formed solid is filtered, washed with water and dried leaving 1.45 g. of 1,4-dimethyl-9,10-dihydro-9,10-anthracenedicarboxaldehyde (m.p. 159°–160° C.).

EXAMPLE 13

1,4-Dimethyl-bis(2-imidazolin-2-ylhydrazone)-9,10-dihydro-9,10-anthracenedicarboxaldehyde dihydrochloride A mixture of 1.15 g. of 1,4-dimethyl-9,10-dihydro-9,10-anthracenedicarboxaldehyde and 1.53 g. of 2-hydrazinoimidazoline dihydrochloride in 50 ml. of n-propanol is boiled and concentrated to 20 ml. over the course of two hours. The resulting solution was treated with one ml. of acetone and 75 ml. of ether giving a pale yellow precipitate which was filtered off, washed with acetone and dried leaving 1.8 g. of product, m.p. 230°–235° C. dec.

EXAMPLE 14

Cis-1,4-dimethoxy-9,10-dihydro-9,10-ethanoanthracene-11,12-diol, cyclic carbonate, syn and anti isomers Fifteen grams of 1,4-dimethoxyanthracene is refluxed under nitrogen with 55 g. of vinylene carbonate for 16 hours. The excess vinylene carbonate is removed under vacuum (55° C./12 mm.) and the residue is slurried in chloroform and filtered retaining 13 g. of a mixture of yellow and colorless crystals. On boiling this mixture with methylene chloride and filtering there is left 10.5 g. of colorless crystals, m.p. 283°–285° C. of one syn or anti isomer of the product.

The other syn or anti isomer is obtained from the original chloroform filtrate by precipitation with methanol and recrystallizing from a mixture of methylene chloride and methanol giving 5 g. of colorless crystals, m.p. 255°–260° C. Both isomers show the same infra-red spectrum, analyze correctly and show a depressed mixed melting point (238°–245° C.).

EXAMPLE 15

Cis-1,4-dimethoxy-9,10-dihydro-9,10-ethanoanthracene-11,12-diol, syn and anti isomers A mixture of 10.5 g. of cis-1,4-dimethoxy-9,10-dihydro-9,10-ethanoanthracene-11,12-diol, cyclic carbonate, m.p. 283°–285° C., and 8.5 g. of potassium hydroxide, 12 ml. of water and 85 ml. of ethanol is stirred at room temperature for 16 hours. The formed solid is filtered, washed with water and dried leaving 5.0 g. of one of the isomers of the product m.p. 187°–188° C.

The other syn/anti isomer is obtained in the same manner from 4.0 g. of the corresponding cyclic carbonate, m.p. 238°–245° C., giving 2.1 g. of product, m.p. 183°–185° C. Both isomeric diols show the same infra-red spectrum, analyze correctly and show a depressed mixed melting point, m.p. 155°–158° C.

EXAMPLE 16

Bis-(2-imidazolin-2-ylhydrazone)-1,4-dimethoxy-9,10-dihydro-9,10-anthracenedicarboxaldehyde dihydrochloride A mixture of 1.5 g. of 1,4-dimethoxy-9,10-dihydro-9,10-anthracenedicarboxaldehyde and 1.8 g. of 2-hydrazino-2-imidazoline dihydrochloride in 100 ml. of n-propanol is boiled and concentrated to 50 ml. over the course of two hours. The cloudy solution is clarified by filtration and then is basified with saturated sodium bicarbonate solution and diluted with three volumes of water yielding 1.5 g. of the free base as a yellow solid, m.p. 235°–240° C. The dihydrochloride salt of the product is obtained by dissolving 1 g. of the free base in 40 ml. of n-propanol and treating with 1 ml. of 7 N anhydrous hydrochloric acid in ethanol. The solution is concentrated to an oil and recrystallized from n-propanol giving 0.3 g. of a colorless dihydrochloride salt m.p. 250°–255° C.

We claim:

1. A compound selected from the group consisting of those of the formula:

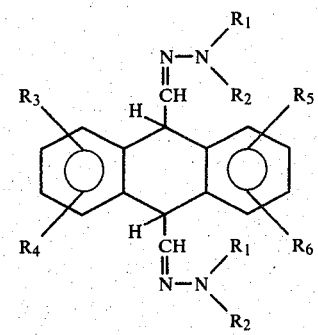

wherein $R_1$ is selected from the group consisting of hydrogen and alkyl having up to 4 carbon atoms; $R_2$ is selected from the group consisting of hydrogen, alkyl having up to 4 carbon atoms, phenyl and monovalent moieties of the formulae:

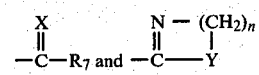

wherein n is 2, 3, 4, or 5, $R_7$ is amino, anilino, hydrazino, monohydroxyalkylamino having from 2 to 4 carbon atoms and wherein the carbon atom alpha to the nitrogen atom may not bear an hydroxy group, alkylamino having up to 4 carbon atoms, dialkylamino wherein each alkyl group has up to 4 carbon atoms, cycloalkylamino having from 3 to 6 carbon atoms, benzylamino, α-phenethylamino, β-phenethylamino, 2-furfurylamino, 3-furfurylamino, α-thenylamino, β-thenylamino, α-pyridylmethylamino, β-pyridylmethylamino, γ-pyridylmethylamino, indanylamino, pyrrolidino, piperidino, morpholino, thiomorpholino, N-methylpiperazino, alkoxy having up to 4 carbon atoms or alkylthio having up to 4 carbon atoms, X is oxo, thioxo, imino or alkylimino having up to 4 carbon atoms, and Y is oxy, thio or a divalent group of the formula:

wherein $R_8$ is hydrogen, alkyl having up to 4 carbon atoms or monohydroxyalkyl having from 2 to 4 carbon atoms and wherein the carbon atom alpha to the nitrogen atom may not bear an hydroxy group; and $R_3$, $R_4$, $R_5$ and $R_6$ are each individually selected from the group consisting of hydrogen, halogen, hydroxy, nitro, amino, sulfonamido, alkyl having up to 4 carbon atoms and alkoxy having up to 4 carbon atoms; and the pharmacologically acceptable acid-addition and quaternary ammonium salts thereof.

2. The compound according to claim 1 wherein $R_1$, $R_3$, $R_4$, $R_5$ and $R_6$ are hydrogen and $R_2$ is

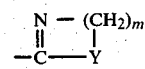

wherein Y is imino and m is two; bis(2-imidazolin-2-yl)hydrazone of 9,10-dihydro-9,10-anthracenedicarboxaldehyde dihydrochloride.

3. The compound according to claim 1 wherein $R_1$, $R_3$, $R_4$, $R_5$ and $R_6$ are hydrogen and $R_2$ is

wherein X is imino and R7 is methylamino; 1,1-[9,10-dihydro-9,10-anthrylenebis(methylidynenitrilo)]bis-3-methylguanidine dihydroiodide.

4. The compound according to claim 1 wherein $R_1$, $R_3$, $R_4$, $R_5$ and $R_6$ are hydrogen and $R_2$ is

wherein X is methylimino and R7 is methylamino; 1,1'-[9,10-dihydro-9,10-anthrylene-bis(methylidynenitrilo)]-bis-(2,3-dimethylguanidine)dihydroiodide.

5. The compound according to claim 1 wherein $R_1$, $R_3$, $R_4$, $R_5$ and $R_6$ are hydrogen and $R_2$ is

wherein X is imino and R7 is hydroxyethylamino; 1,1'-[9,10-dihydro-9,10-anthrylenebis(methylidynenitrilo)]-bis-(3,3-dimethylguanidine)dihydroiodide.

6. The compound according to claim 1 wherein $R_1$, $R_3$, $R_4$, $R_5$ and $R_6$ are hydrogen and $R_2$ is

wherein X is imino and R7 is hydroxyethylamino; 1,1'-[9,10-dihydro-9,10-anthrylenebis(methylidynenitrilo)]-bis-[3-(2-hydroxyethyl)guanidine]dihydroiodide.

7. The compound according to claim 1 wherein $R_1$, $R_3$, $R_4$, $R_5$ and $R_6$ are hydrogen and $R_2$ is

wherein X is imino and R7 is amino; 1,1'-[9,10-dihydro-9,10-anthrylenebis(methylidynenitrilo)]diguanidine dihydrochloride.

8. The compound according to claim 1 wherein $R_1$, $R_3$, $R_4$, $R_5$ and $R_6$ are hydrogen and $R_2$ is

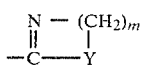

wherein Y is imino and m is three; bis(1,4,5,6-tetrahydro-2-pyrimidin-2-ylhydrazone) of 9,10-dihydro-9,10-anthracenedicarboxaldehyde dihydrochloride.

9. The compound according to claim 1 wherein $R_1$ is methyl, $R_3$, $R_4$, $R_5$ and $R_6$ are hydrogen and $R_2$ is

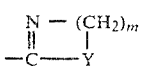

wherein Y is imino and m is two; bis(2-imidazlin-2-ylmethylhydrazone) of 9,10-dihydro-9,10-anthracenedicarboxaldehyde dihydroiodide.

10. The compound according to claim 1 wherein $R_1$, $R_3$, $R_4$, $R_5$ and $R_6$ are hydrogen and $R_2$ is

wherein X is imino and R7 is benzylamino; 1,1'-[9,10-dihydro-9,10-anthrylenebis)methylidynenitrilo)]bis(3-benzylguanidine)dihydroiodide.

11. The compound according to claim 1 wherein $R_1$, $R_3$, $R_4$, $R_5$ and $R_6$ are hydrogen and $R_2$ is

wherein X is thio and R7 is imino; 9,10-dihydro-9,10-anthracenedicarboxaldehyde bis(thiosemicarbazone).

12. The compound according to claim 1 wherein $R_1$, $R_3$, $R_4$, $R_5$ and $R_6$ are hydrogen and $R_2$ is

wherein X is imino and R7 is cyclohexylamino; 1,1'-[9,10-dihydro-9,10-anthrylenebis(methylidynenitrilo)]-bis(3-cyclohexylguanidine)dihydroiodide.

13. The compound according to claim 1 wherein $R_1$, $R_3$, $R_4$, $R_5$ and $R_6$ are hydrogen and $R_2$ is

wherein X is imino and R7 is morpholino; N,N'-[9,10-dihydro-9,10-anthrylenebis(methylidynenitrilo)]di(4-morpholinecarboxamidine)dihydroiodide.

14. The compound according to claim 1 wherein $R_1$, $R_3$, $R_4$, $R_5$ and $R_6$ are hydrogen and $R_2$ is

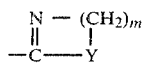

wherein m is 2 and Y is 2-hydroxypropylimino; bis[2-(2-hydroxypropyl)-2-imidazolin-2-ylhydrazone) of 9,10-dihydro-9,10-anthracenedicarboxaldehyde dihydroiodide.

15. The compound according to claim 1 wherein $R_1$, $R_3$, $R_4$ and $R_6$ are hydrogen, $R_5$ is 2-chloro and $R_2$ is

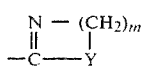

wherein Y is imino and m is two; bis(2-imidazolin-2-ylhydrazone) of 2-chloro-9,10-dihydro-9,10-anthracenedicarboxaldehyde dihydrochloride.

16. The compound according to claim 1 wherein $R_1$, $R_3$, $R_4$ and $R_6$ are hydrogen, $R_5$ is 2-methyl and $R_2$ is

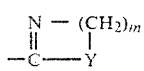

wherein Y is imino and m is two; bis(2-imidazolin-2-ylhydrazone) of 2-methyl-9,10-dihydro-9,10-anthracenedicarboxaldehyde dihydrochloride.

17. The compound according to claim 1 wherein R<sub>5</sub> is 1-hydroxy, R<sub>6</sub> is 4-hydroxy, R<sub>1</sub>, R<sub>3</sub> and R<sub>4</sub> are hydrogen and R<sub>2</sub> is

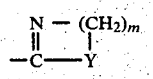

wherein Y is imino and m is two; bis(2-imidazolin-2-ylhydrazone) of 1,4-dihydroxy-9,10-dihydro-9,10-anthracenedicarboxaldehyde dihydrochloride.

18. A compound selected from the group consisting of those of the formula:

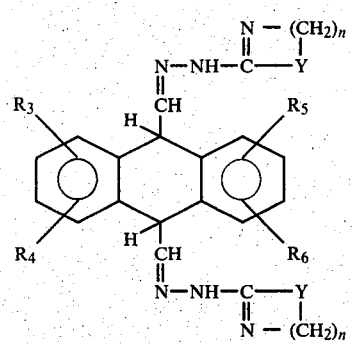

wherein n is 2, 3, 4 or 5; Y is oxy, thio or a divalent group of the formula:

wherein R<sub>8</sub> is hydrogen, alkyl having up to 4 carbon atoms or monohydroxyalkyl having from 2 to 4 carbon atoms and wherein the carbon atom alpha to the nitrogen atom may not bear an hydroxy group; and R<sub>3</sub>, R<sub>4</sub>, R<sub>5</sub> and R<sub>6</sub> are each individually selected from the group consisting of hydrogen, halogen, hydroxy, nitro, amino, alkyl having up to 4 carbon atoms and alkoxy having up to 4 carbon atoms; and the pharmacologically acceptable acid-addition and quaternary ammonium salts thereof.

19. A compound selected from the group consisting of those of the formula:

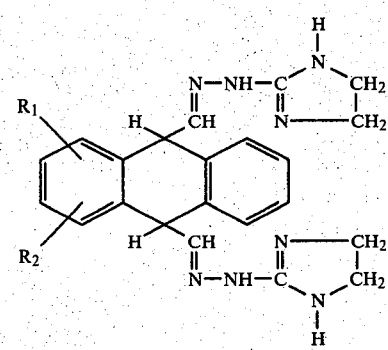

wherein R<sub>1</sub> and R<sub>2</sub> are each individually selected from the group consisting of hydrogen, hydroxy, fluoro, chloro, alkyl having up to 3 carbon atoms and alkoxy having up to 3 carbon atoms; and the pharmacologically acceptable acid-addition and quaternary ammonium salts thereof.

* * * * *